(12) United States Patent
Thomas et al.

(10) Patent No.: US 7,886,740 B2
(45) Date of Patent: Feb. 15, 2011

(54) GAS SYSTEMS AND METHODS FOR ENABLING RESPIRATORY STABILITY

(75) Inventors: Robert J. Thomas, Newton, MA (US); Robert W. Daly, Weston, MA (US)

(73) Assignee: Beth Israel Deaconess Medical Center, Inc., Boston, MA (US)

(*) Notice: Subject to any disclaimer, the term of this patent is extended or adjusted under 35 U.S.C. 154(b) by 2219 days.

(21) Appl. No.: 10/716,360

(22) Filed: Nov. 18, 2003

(65) Prior Publication Data

US 2004/0144383 A1 Jul. 29, 2004

Related U.S. Application Data

(60) Provisional application No. 60/443,227, filed on Jan. 28, 2003.

(51) Int. Cl.
- A61M 15/00 (2006.01)
- A61M 16/00 (2006.01)
- A62B 7/00 (2006.01)

(52) U.S. Cl. ............... 128/204.23; 128/204.18; 128/204.21; 128/205.11; 128/205.17; 128/203.12; 128/914

(58) Field of Classification Search ........... 128/204.23, 128/204.21, 204.18, 205.11, 205.17, 203.12, 128/914

See application file for complete search history.

(56) References Cited

U.S. PATENT DOCUMENTS

| | | | |
|---|---|---|---|
| 4,188,946 A | | 2/1980 | Watson et al. |
| 5,320,093 A | * | 6/1994 | Raemer .......... 128/203.12 |
| 5,957,129 A | * | 9/1999 | Tham et al. ......... 128/204.28 |
| 5,975,078 A | * | 11/1999 | Pauley .............. 128/205.23 |
| 6,029,660 A | | 2/2000 | Calluaud et al. |
| 6,041,777 A | * | 3/2000 | Faithfull et al. ....... 128/200.24 |
| 6,269,811 B1 | | 8/2001 | Duff et al. |
| 6,306,098 B1 | | 10/2001 | Orr et al. |

(Continued)

FOREIGN PATENT DOCUMENTS

WO   WO97/10869   9/1996

(Continued)

OTHER PUBLICATIONS

Lorenzi-Filho, G. et al., "Effects of Inhaled Carbon Dioxide and Oxygen on Cheyne-Stokes Respiration in Patients with Heart Failure," *American Journal of Respiratory Critical Care Medicine* 159:1490-1498 (1999).

(Continued)

*Primary Examiner*—Patricia M Bianco
*Assistant Examiner*—Nihir Patel
(74) *Attorney, Agent, or Firm*—Hamilton, Brook, Smith & Reynolds, P.C.

(57) ABSTRACT

Minimal concentrations of $CO_2$ are mixed with pressurized air to provide a gas mix effective for stabilizing breathing of target patients or users. $CO_2$ concentrations below about 2% and preferably between about 0.5% and 1.25% are employed. A gas modulator includes a gas mixing module, a sensor and a control processor. The gas mixing module mixes plural gases, including $CO_2$, into a gas mix, for delivery to a substantially leak-proof patient face mask. The sensor, located substantially at the face mask, measures $CO_2$ concentration in the face mask. The control processor, based on a signal from the sensor, controls the $CO_2$ concentration in the gas mix.

14 Claims, 5 Drawing Sheets

U.S. PATENT DOCUMENTS

2002/0059933 A1     5/2002     Jaffe et al.
2002/0185129 A1    12/2002     Fisher et al.

FOREIGN PATENT DOCUMENTS

WO         WO 00/45882       8/2000

OTHER PUBLICATIONS

Javaheri, S. and W.S. Corbett, "Association of Low $PaCO_2$ with Central Sleep Apnea and Ventricular Arrhythmias in Ambulatory Patients with Stable Heart Failure," *Annals of Internal Medicine* 128:204-207, Feb. 1, 1998.

Xie, A. et al., "Apnea-Hypopnea Threshold for $CO_2$ in Patients with Congestive Heart Failure," *American Journal of Respiratory Critical Care Medicine* 165(9):1245-50, May 1, 2002.

Topor, Z.L. et al., "Dynamic ventilatory response to CO(2) in congestive heart failure patients with and without central sleep apnea," *J. Appl. Phys.* 91(1):408-16, Jul. 2001.

Nattie, E., "$CO_2$, Brainstem Chemoreceptors and Breathing," *Progress in Neurobiology* 59(4):299-331, Nov. 1999.

Javaheri, S., "A Mechanism of Central Sleep Apnea in Patients with Heart Failure," *The New England Journal of Medicine* 341(13):949-54, Sep. 23, 1999.

Xie, A. et al., "Effects of inhaled CO2 and added dead space on idiopathic central sleep apnea," *J. Appl. Physiol.*, 82(3):918-26, Mar. 1997.

Xie, A. et al., "Hypocapnia and Increased Ventilatory Responsiveness in Patients with Ideopathic Central Sleep Apnea," *American Journal of Respiratory and Critical Care Medicine, 152(6 Pt 1)*: 1950-5, Dec. 1995.

Badr, M.S. "Treatment of Refractory Sleep Apnea with Supplemental Carbon Dioxide," *American Journal of Respiratory and Critical Care Medicine* 150(2):561-4, Aug. 1994.

Thalhofer S. and P. Dorow, "Sleep-Breathing Disorders and Heart Failure," *Sleep and Breathing* 4:(3)103-111, 2000.

Teschler, H. et al., "Adaptive Pressure Support Servo-Ventilation: A Novel Treatment for Cheyne-Stokes Respiration in Heart Failure," *American Journal of Respiratory Critical Care Medicine* 164:614-619, 2001.

Krachman S.L. et al., "Comparison of Oxygen Therapy with Nasal Continuous Positive Airway Pressure on Cheyne-Stokes Respiration During Sleep in Congestive Heart Failure," *Chest* 116:1550-1557, 1999.

Lorenzi-Filho, G. et al., "Effects of Inhaled Carbon Dioxide and Oxygen on Cheyne-Stokes Respiration in Patients with Heart Failure," *American Journal of Respiratory Critical Care Medicine* 159:1490-1498, 1999.

Pack A.I. et al., "Modafinil as Adjunct Therapy for Daytime Sleepiness in Obstructive Sleep Apnea," *American Journal of Respiratory Critical Care Medicine* 164:1675-1681, 2001.

Francis, D.P. et al., "Quantitative General Theory for Periodic Breathing in Chronic Heart Failure and its Clinical Implications," *Circulation* 102(18):2214-2221, Oct. 31, 2000.

* cited by examiner

GAS SYSTEMS AND METHODS FOR ENABLING RESPIRATORY STABILITY

RELATED APPLICATIONS

This application claims the benefit of U.S. Provisional Application No. 60/443,227, filed on Jan. 28, 2003, the entire teachings of which are incorporated herein by reference

BACKGROUND OF THE INVENTION

Patients with sleep disordered breathing (SDB) have variable contributions from upper airway obstruction and abnormal control of breathing. The latter is best demonstrated by Cheyne-Stokes respiration (e.g., in congestive cardiac failure), but a lesser degree of periodic breathing is a common finding in clinical practice. See reference [1] below. The greater the contribution from abnormal control, the less effective are therapies based on air pressure support of the upper airway, such as continuous or bilevel positive airway pressure (xPAP). See reference [2] below. Additional oxygen is a commonly used therapeutic adjunct, even if hypoxia is not severe, but does not fully treat periodic breathing. See reference [3] below.

It has been known for over fifty years that disordered carbon dioxide homeostasis in the blood is fundamental to the development of periodic breathing patterns. It has also been known that increasing the concentration of $CO_2$ in inspired air by 2-6% has a profound and immediate stabilizing effect on respiration during sleep (see reference [4] below). Supplemental $CO_2$ stabilizes breathing by damping the variations in $CO_2$ concentration in the blood caused by hyperventilation and hypoventilation, and by increasing the average partial pressure of $CO_2$ in the blood. Nevertheless, the practical difficulty of using $CO_2$, along with the development of xPAP technology, has resulted in little clinical interest in developing methods of improving sleep-breathing quality through its use. The use of xPAP technology together with carbon dioxide presents even more difficult practical problems.

Many SDB patients who are treated with xPAP have residual symptoms. The resulting sleep fragmentation is considered clinically important. See reference [5] below. While xPAP therapy is often highly effective in treating non-complex obstructive SDB, patients with more complex disease usually fail xPAP therapy. Such patients typically have evidence of overt or subtle periodic breathing and may have a mix of obstructive apneas, hypopneas and central apneas. Often, these patients will be more unstable during non-REM versus REM sleep. Even with the addition of oxygen to PAP these patients as a group are very difficult to treat.

There are three major populations with difficult-to-control SDB within the context of periodic breathing: 1) Patients with congestive cardiac failure or renal failure and overt Cheyne-Stokes respiration; 2) Patients with overt Cheyne-Stokes respiration but no heart failure or renal failure; and 3) Patients with more subtle but important degrees of periodic breathing (no pure Cheyne-Stokes respiration), with or without heart/renal failure. The majority of patients with difficult-to-control SDB currently seen in sleep clinics may fall into this latter category.

Each of the references below is incorporated herein by reference:

1. Thalhofer S., Dorow P. Sleep-Breathing Disorders and Heart Failure. Sleep Breath 2000;4:103-112.

2. Teschler H., Dohring J., Wang Y. M., Berthon-Jones M. Adaptive pressure support servo-ventilation: a novel treatment for Cheyne-Stokes respiration in heart failure. Am J Respir Crit Care Med 2001;164:614-619.

3. Krachman S. L., D=Alonzo G. E., Berger T. J., Eisen H. J. Comparison of oxygen therapy with nasal continuous positive airway pressure on Cheyne-Stokes respiration during sleep in congestive heart failure. Chest 1999;116:1550-1557.

4. Lorenzi-Filho G., Rankin F., Bies I., Douglas, Bradley T. Effects of inhaled carbon dioxide and oxygen on cheyne-stokes respiration in patients with heart failure. Am J Respir Crit Care Med 1999;159:1490-1498.

5. Pack A. I., Black J. E., Schwartz J. R., Matheson J. K. Modafinil as adjunct therapy for daytime sleepiness in obstructive sleep apnea. Am J Respir Crit Care Med 2001; 164:1675-1681.

SUMMARY OF THE INVENTION

There is a clinical need to improve respiratory stability in patients with SDB, besides controlling the obstruction. An effective therapy will improve quality of life and cognitive function, and there is increasing evidence that survival of patients with heart failure may be improved by control of SDB.

The inventors of the present invention have re-visited the use of carbon dioxide ($CO_2$) as a sleep-breathing stabilizer by designing and testing (for safety and efficacy) a prototype device that can provide precise concentrations of $CO_2$ and oxygen ($O_2$). The prototype device is designed to operate in conjunction with existing xPAP equipment, although it may be used alone or with other treatment modalities. Thus generally speaking, the present invention provides (i) a substantially low concentration carbon dioxide and pressurized air gas mix, and (ii) a device for stabilizing breathing using the pressurized air and carbon dioxide gas mix delivered to a patient centric ventilatory space module (PCVSM) for use (inhalation) by a target. Concentration of $CO_2$ in the gas mix is less than 2% and preferably between about 0.5% and 1.25%.

A prototype and first embodiment of the present invention includes a mobile (selectably moveable) cart or other suitable housing, on which are installed (i) a $CO_2$ source, (ii) a gas-mixing chamber or module receiving the source $CO_2$, as well as $O_2$ from a separate oxygen concentrator, (iii) $CO_2$ and $O_2$ monitors on the output side of the gas-mixing module, and (iv) a control processor with appropriate software and display system, coupled to receive signals from the monitors and sensors via a multi-function input box and coupled to control input and output valves of the gas-mixing module. Further, an electrically actuated proportional valve, controlled by the control processor, is employed between the $CO_2$ source and gas mixing module, or in the gas mixing module.

A limiting orifice consisting of a needle valve is placed in series with the proportional valve and provides for a maximum flow rate and thus concentration of $CO_2$.

In accordance with one aspect of the present invention, the system offers redundant $CO_2$ monitoring capability as well as $O_2$ monitoring. The flow of $CO_2$ into the gas mixing chamber is controlled by a calibrated electrically actuated proportional valve, and is measured by a visually readable variable area glass flow meter. The actual concentration of $CO_2$ in the mixing chamber is measured by a patient monitor such as a Datex/Ohmeda Capnomac monitor incorporating both $CO_2$ and $O_2$ sensors, and the final concentration of $CO_2$ at the patient interface is measured using a mainstream $CO_2$ sensor such as the Nihon Kohden TG951T $CO_2$ sensor. The Nihon Kohden sensor also provides a value for end-tidal $CO_2$ (etCO2), thought to be the most direct measure of $CO_2$ concentration in the alveoli of the lungs. The purpose of the multiple redundant sensors is to ensure the safe delivery of appropriate concentrations of CO2 and oxygen to the patient.

The monitoring of gas concentrations is further enhanced by the incorporation of a sensor that directly measures gas concentrations in the patient's blood. A transcutaneous monitor, such as a Sensormedics Microgas 7650, provides measurement of the partial pressure of both oxygen and CO2 in the patient's arterial blood The parts, i.e., connectors, tubes, pipes, are assembled in a modular tray or box that can bolt in or out of the rack. A patient monitor unit, such as a Datex/Ohrneda Capnomac unit, is calibrated and provides, but is not limited to, analog and digital waveforms such as the following: a) Analog: CO2 waveform and O2 waveform (0 v to +10 v); b) Digital: Inspired CO2, etCO2, Inspired O2, Alarm States, Time, Ambient Pressure.

The "normally off" proportional valve is preferably a stainless steel or brass proportional valve that controls flow of the CO2 supply to the gas mixing chamber. The valve is energized via a power voltage from a power supply and by a control voltage, which is generated by the control processor, or in a prototype embodiment, from a computer running the DASYLab (see www.dasylab.net/dasylab_english) data acquisition system.

A multi-function input box is preferably a signal box built with a signal input card. One example, built by IOTech (www.iotech.com), has sixteen single-ended analog inputs, of which eight are single-ended inputs available via screw connectors.

The software used for display and for providing an experimental workspace is DASYLab (Data Acquisition System Laboratory) running on a P4 computer with 1 GB SDRAM and over 80 GB hard drive space. A basic set of screens/ worksheets for operating the machine have been created, under which the data from the gas mixing module are monitored, alarms are triggered, the CO2 supply valve is adjusted and the whole session is recorded. A patient monitoring screen records CO2 as detected at the patient delivery end (e.g., facemask) and displays the values on the screen in real time.

A standard xPAP unit connects to the input side of the gas-mixing module via standard respiratory tubing. Standard respiratory tubing leading from the output side of the gas mixing module is led to the patient, with an optional heated humidifier interposed between the system and the patient. The tubing is connected to a "Y" connector, one of the other legs of the "Y" connector being attached to a length of standard respiratory tubing, the exhaust tubing. The exhaust tubing returns to the system via an exhaust port on the front of the mixing module, where the exhaust bleed rate is controlled by a variable orifice comprising a manually operated needle valve or a processor controlled proportional valve, or the like. The third part of the "Y" connector is attached to the detector module of the Nihon Kohden sensor. The Nihon Kohden sensor is attached to a substantially sealed oronasal or nasal xPAP mask. The purpose of this configuration is to avoid dilution of the exhaled CO2 before it is measured by the Nihon Kohden sensor, thus permitting accurate measurement of etCO2.

In other embodiments, the output of the gas mixing module can be connected to other patient-centric ventilatory space modules (PVCSM's) such as an incubator, an unsealed mask, a tent or a nasal canula.

One or more pneumotachographs are optionally inserted into the breathing circuit at various locations, including the hose connecting the system to the "Y" fitting, between the "Y" fitting and the Nihon Kohden sensor, or between the "Y" fitting and the exhaust port on the system. Each pneumotachograph is connected via specialized tubing to a dedicated pressure transducer, the voltage output of which is proportional to the flow rate of gas through the pneumotachograph. The voltage from the pressure transducer is read by the system controller and is recorded. The purpose of the pneumotachographs is to measure either or both of, system operating parameters such as air flow through the mixing chamber, exhaust bleed rate, or patient physiological parameters, particularly respiration. These data may be used to control various operating parameters of the system.

Accordingly, a gas modulator, a gas regulator or other gas delivery system, according to an embodiment of the present invention, includes a gas mixing module (generally gas mixing means), a sensor and a control processor. The gas mixing module mixes plural gases, including a first gas such as carbon dioxide (CO2), into a gas mix, for delivery to a substantially leak-proof patient centric ventilatory space module (PCVSM), such as an incubator; a tent; a facemask; and a nasal cannula. A sensor, located substantially at the PCVSM, measures concentration of the first gas in the PCVSM. The control processor, based on a signal from the sensor, controls the concentration of the first gas in the gas mix.

The first gas may be supplied from a pressurized source, and the gas modulator may further include a control valve module, which regulates flow of the first gas from the pressurized source to the gas mixing module, in response to a control signal from the control processor. The control valve module may be, for example, a normally-off solenoid valve, or a proportional valve. A limiting orifice may be arranged in series with the control valve.

The gas mixing module consists of a small box (mixing chamber) having an input plenum, an output plenum and a flow channel which connects the input plenum to the output plenum. The three chambers are formed by a T-shaped baffle in one embodiment.

A flow meter on the input side of the gas mixing module provides a visual and/or electrical indication of flow of the first gas into the gas mixing module.

Similarly, a flow meter on the output side provides a visual and/or electrical indication of flow of bleed air vented from the PCVSM. Further, the gas modulator may contain a proportional valve that is responsive to a control signal from the control processor, which regulates exhaust bleed air vented from the PCVSM. The control processor can thus dynamically control the proportional valve in response to detected system changes, such as physical changes in the mask seal. Alternatively, bleed air may be controlled via a manually operated needle valve. Pressurized air may be a second gas with which the first gas is mixed. The gas modulator may further include a positive airway pressure (PAP) module that produces the pressurized air, the pressurized air being delivered from the PAP module to the gas mixing module via a tube.

The control processor may be additionally responsive to patient state information from any combination of: thermistors, strain gauges, pneumotachographs and physiological signals, including for example, EEG and EKG signals.

The gas modulator may further include any or all of, but is not limited to: a transcutaneous blood gas monitor that measures partial pressure, in a patient, of one or more gases, including the first gas; a pressure sensor, mounted in proximity to the PCVSM, that measures inspired and expired breath volume; a skin conductance monitor that measures skin conductance; and an arterial contraction monitor that monitors the state of contraction of small arteries in a patient's finger. Each of these devices provides a signal to the control processor, which uses the information to determine and/or control the concentration of the first gas in the gas mix.

A display monitor may be connected to the control processor, so that the control processor can display, for example, an indicator that indicates the actual concentration of at least the first gas as sampled from the gas mixing module. For example, a first indicator may show the concentration of $CO_2$, while a second indicator shows the concentration of $O_2$. Further, a scrolling chart recorder may be displayed to indicate the value of at least one parameter of interest, including, but not limited to: $CO_2$ concentration; $O_2$ concentration; control processor control state; a sensor signal; or a physiological signal.

An embodiment of the gas modulator includes a remote interface through which the control processor is remotely controllable from a remote workstation. The connection to the remote workstation may be, for example, a wireless TCP/IP connection, or may be wired, or may use another protocol.

The gas modulator can also include an audio recording and analysis module to record and analyze audio signals from one or more microphones attached to a patient.

A gas sampling sensor can monitor the concentration of one or more gases, including the first gas, within the gas mixing module. The gas sampling sensor provides a signal to the control processor, which the control processor analyzes in controlling the concentration of the first gas in the gas mix. For example, the gases may be carbon dioxide ($CO_2$) and oxygen ($O_2$).

In at least one embodiment, an input flow sensor measures flow of the first gas into the gas mixing module. The input flow sensor provides a signal to the control processor, which analyzes the signal to control the concentration of the first gas in the gas mix.

A PCVSM bleed air sensor can measure flow of PCVSM bleed air. The PCVSM bleed air sensor provides a signal to the control processor, which analyzes the signal to control the concentration of the first gas in the gas mix.

One or more pneumotachographs, connected to pressure transducers, measure air flow in various parts of the breathing circuit, such as air flow through the mixing chamber, exhaust air, and patient respiration. Output from the pressure transducers is proportional to air flow and is read by the control processor. In one embodiment, a pneumotachograph can be placed within the mixing chamber itself between the input plenum and the output plenum.

In one embodiment, the control processor continuously receives and analyzes incoming data and indicates an alarm condition based on the incoming data and one or more of the following (and possibly other) parameters: maximum $CO_2$ flow; maximum $CO_2$ concentration in the mixing chamber, maximum inspired $CO_2$; maximum arterial $CO_2$; and maximum end-tidal $CO_2$. Delivery of $CO_2$ is reduced or halted when an alarm condition is present. Furthermore, a visual or audible alarm may be sounded when an alarm condition is present.

In one embodiment, the PCVSM consists of a substantially sealed oronasal or nasal xPAP mask which is designed to eliminate dilution of exhaled air so that accurate measurements of $CO_2$ concentrations in exhaled air can be made.

The control processor can thus determine, from the sensor located substantially at the PCVSM, end-tidal $CO_2$ concentration (that is, the $CO_2$ concentration just as the patient finishes exhaling) as well as inspired $CO_2$ concentration, the average $CO_2$ concentration as the patient breathes in. et $CO_2$ concentration provides data about the patient's blood levels of $CO_2$. Inspired $CO_2$ concentration indicates the level of $CO_2$ that the inventive device is delivering.

The control processor can thus control the concentration of $CO_2$ for a variety of patients, including those diagnosed as having sleep disordered breathing (SDB) or Cheyne-Stokes respiration, those diagnosed as having had an "Apparent Life Threatening Experience" (ALTE), and those diagnosed as having apnea of prematurity.

An embodiment of the gas modulator of the present invention includes a memory for recording a history of data/signals received by the control processor and control signals generated by the control processor.

One embodiment of the gas modulator is intended for a non-clinical setting. The first incoming gas may be contained in a canister having an orifice of a size which determines maximum flow according to a specified limit. This embodiment may further include recording and reporting means, which maybe remotely accessible, for example, via a dial-up connection.

In yet another embodiment, $CO_2$ is generated by accumulating the patient's own $CO_2$ in a deadspace. A valve is regulated to adjust the $CO_2$ concentration in the deadspace from which the patient is breathing. This embodiment may comprise a carbon dioxide regulator which includes a positive air pressure (PAP) module, a sensor, and a control processor. The PAP module delivers pressurized air to a substantially leak-proof mask to be worn by a patient. The sensor, located substantially at the patient mask, measures concentration of carbon dioxide in the mask, the concentration dynamically changing in response to the patient's breathing. The control processor receives signals from the sensor and, based on a signal from the sensor, controls an exhaust vent (via, for example, a proportional valve) connected to the mask to control the level of carbon dioxide in the mask.

According to the foregoing, in its most basic form the present invention provides the combination PAP (pressurized air) and low concentration $CO_2$ (less than 2% and preferably about 0.5% to about 1.25%) for effecting respiratory stability (as a method of treatment, a device/machine/system, a gas product and/or a computer program product) heretofore unachieved by the prior art.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A description of preferred embodiments of the invention follows.

A prototype of an embodiment of the present Positive Airway Pressure Gas Modulator (PAPGAM) invention has been built as an investigational medical device, the purpose of which is to deliver precisely metered doses of carbon dioxide gas (CO2), oxygen (O2), and potentially other inhalational agents to patients who are also being treated with positive airway pressure (PAP).

The PAPGAM was designed to meet the need for such an instrument in treatment of unstable breathing, including sleep apnea, periodic breathing and central apnea. These conditions affect millions of people worldwide and result in substantial morbidity and mortality.

Although the stabilizing properties of CO2 and oxygen are documented, the stabilizing properties at low doses (less than 2%) when given in conjunction with PAP as discovered by Applicants are heretofore not well documented or known. No equipment is currently available to deliver CO2 and pressurized air in precisely metered combinations, either in a clinical or home setting.

Precise metering of these gases is essential for therapeutic use since both gases, and especially CO2, have the potential for adverse side effects if an overdose is given. Metering must be maintained over a range of demand conditions. In addition, there may be clinical utility to varying the dosage over time as a function of the physiological response of the patient. As a result, closed loop control based on physiological data obtained from the patient in real time is a unique feature of an embodiment of the PAPGAM invention.

Further Applicants have discovered that the stabilizing effects of CO2 can be achieved at the safer (much reduced risk of overdose) low concentrations of about 0.5% to about 1.25% by mixing CO2 and pressurized air. There is a synergistic effect of combining pressurized air with the subject CO2. Prior to Applicants' discovery of such, use of CO2 was not considered effective in doses below a concentration of 2%. At the newly discovered lower doses/concentrations of CO2, there are numerous advantages including avoidance of adverse side effects, greater safety, patient tolerability and logistical benefits (e.g., enable to employ in an open or closed loop system). As such, a variety of efficacious systems combining PAP with CO2 at the lower concentrations (for example, 0.5%-1.25% or generally below 2%) will be in the purview of one skilled in the art given the principles of the present invention as described next in preferred and alternate embodiments (intended for purposes of illustration and not limitation).

Input Side

Figure 1:
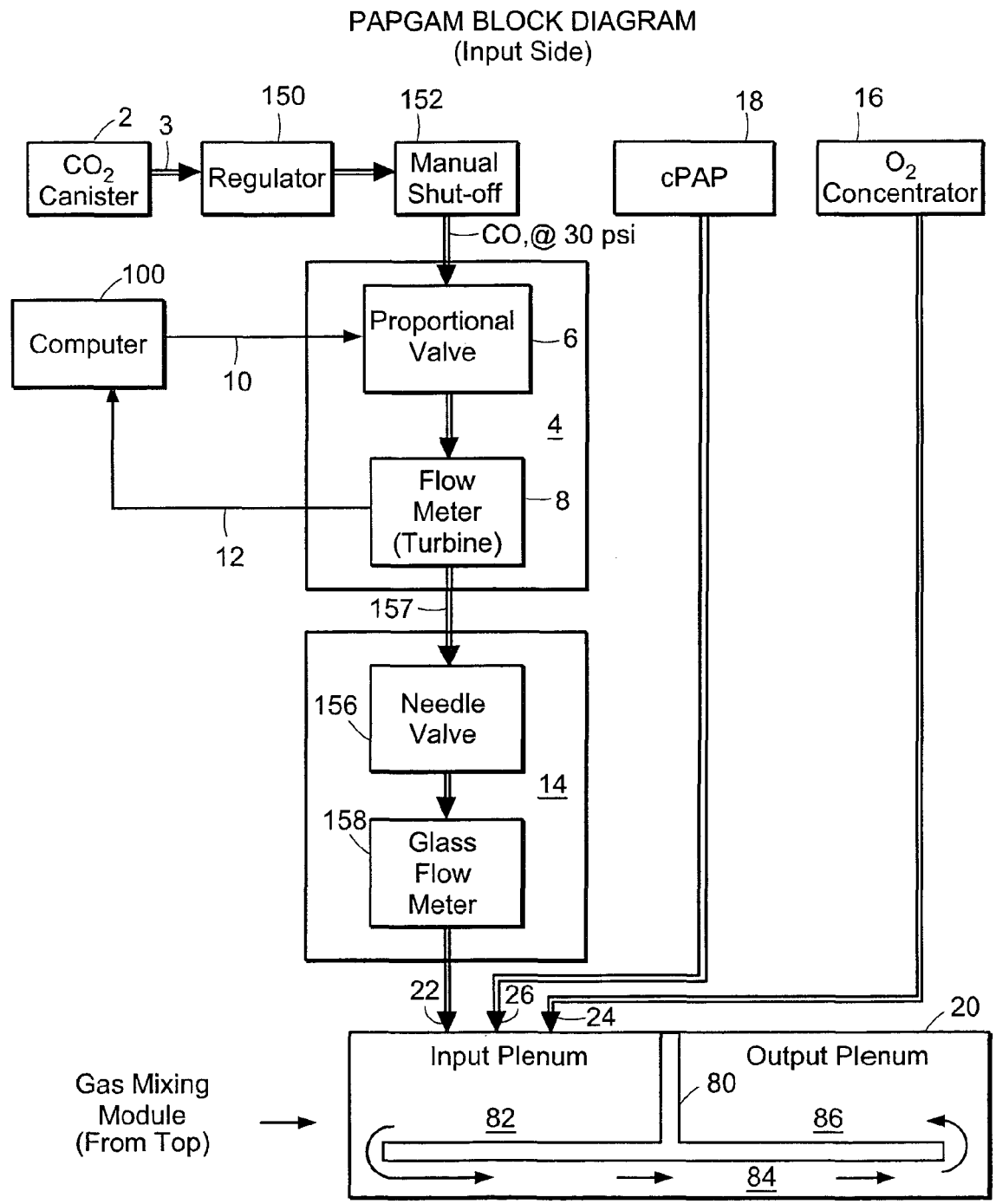
FIG. 1 is a schematic diagram of the input side of an embodiment of the present invention.

FIG. 1 is a schematic diagram of the input side of an embodiment of the invention.

CO2 Source

A CO2 gas source consists of a pressurized canister 2 of medical grade CO2 gas; for example, a five-pound steel canister that may be mounted on the side of the PAPGAM rack. The pressure from the canister is regulated to an appropriate delivery value (approximately 10-40 PSIG) by virtue of an adjustable dual indicator mechanical pressure regulator 150 that is attached directly to the outlet 3 of the canister 2. A lever-operated shut-off valve 152 enables manual cut-off of the CO2 supply.

Control Valve Module

The control valve module 4 modulates the flow of CO2 gas in response to a control signal 10. The module 4 includes a valve 6, for example a Pneutronics VSO electrically-actuated proportional valve, which is energized by DC current 155 at 12V and a 0V-10V control signal 10 from the control processor 100. The control voltage determines the size of the effective orifice of the proportional valve 6 and thus the flow of CO2. When the control voltage is less than one volt or the supply of current is completely interrupted, no CO2 can flow through the valve 6. The input orifice of the valve 6 is connected to the manual shut-off valve 152 by an appropriate length of medical grade tubing.

In the preferred embodiment, the control valve module 4 is fabricated and mounted in a polycarbonate enclosure to further provide isolation from the chassis of the instrument.

In an alternate embodiment, the control valve 6 comprises a "normally off" solenoid valve that permits binary (on-off) control of CO2 according to a control signal 10 received from the control processor 100.

Figure 3:
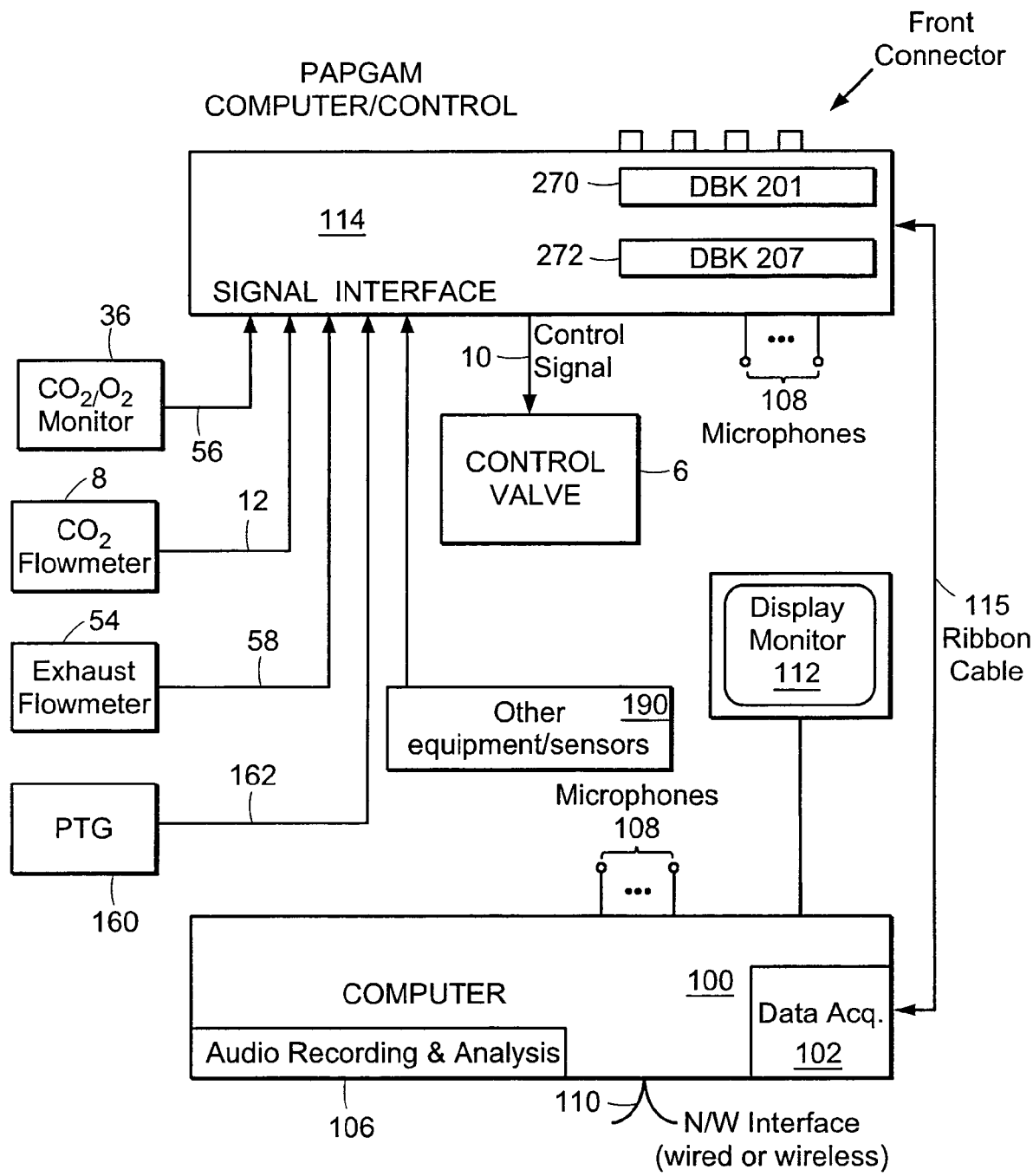
FIG. 3 is a schematic diagram of the control processor system of an embodiment of the present invention.

The output orifice of the valve 6 is connected by tubing to a turbine-type flow meter 8 which measures the amount of CO2 leaving the control valve 6. The flow meter 8 outputs a variable analog voltage signal 12 that is proportional to the flow. This signal 12 is electrically routed to the control processor 100 via signal interface 114 (FIG. 3).

Input Mechanical Flow Controller/Indicator

A mechanical flow controller/indicator 14, comprising (i) a variable area glass flow indicator 158, allows visual measuring of CO2 flow, and (ii) a manually operated needle valve 156 which determines a maximum flow rate of CO2 when the proportional valve 6 is fully open. In one embodiment of the present invention, this controller/indicator 14 is mounted at the input side of the gas mixing module 20, described below. Its input orifice is connected to the valve control module 4 via a short length of tubing 157. Its output orifice is ducted directly into orifice 22 of the input plenum 82 of the gas mixing module 20.

Gas Mixing Module

The gas mixing module 20 mixes pressurized air supplied from a medical positive airway pressure device (xPAP) 18 with the CO2 gas delivered from the valve control module 4, and with oxygen (O2) delivered from an appropriate source 16, such as an oxygen concentrator or bottled oxygen. In one embodiment, the gas mixing module 20 consists of a polycarbonate box approximately 10 cm H 10 cm H 20 cm which contains a T-shaped internal baffle 80.

The baffle 80 creates three connected spaces within the gas mixing module 20. These three spaces include an input plenum 82, a flow channel 84 and an output plenum 86. All incoming gases are conducted into the input plenum 82 via orifices 22, 24, 26. The flow channel 84 connects the input plenum 82 to the output plenum 86. The output plenum 86 provides various outlets (see FIG. 2) through which the mixed gases (i.e., the gas mix) exit the gas mixing module 20.

In the prototype, the gas mixing module 20 is mounted to a 19" rack mount aluminum faceplate. The faceplate is drilled to accommodate mounting screws for the polycarbonate box as well as the various fittings appropriate to each orifice, including, on the input side: a standard green plastic nipple fitting 24 to which the oxygen supply 16 is connected; and a standard 22 mm male fitting 26 for hose connection to the xPAP 18. The entire unit is mounted as an assembly to the PAPGAM cart (housing) via four screws through the 19" faceplate.

Output Side

Figure 2:
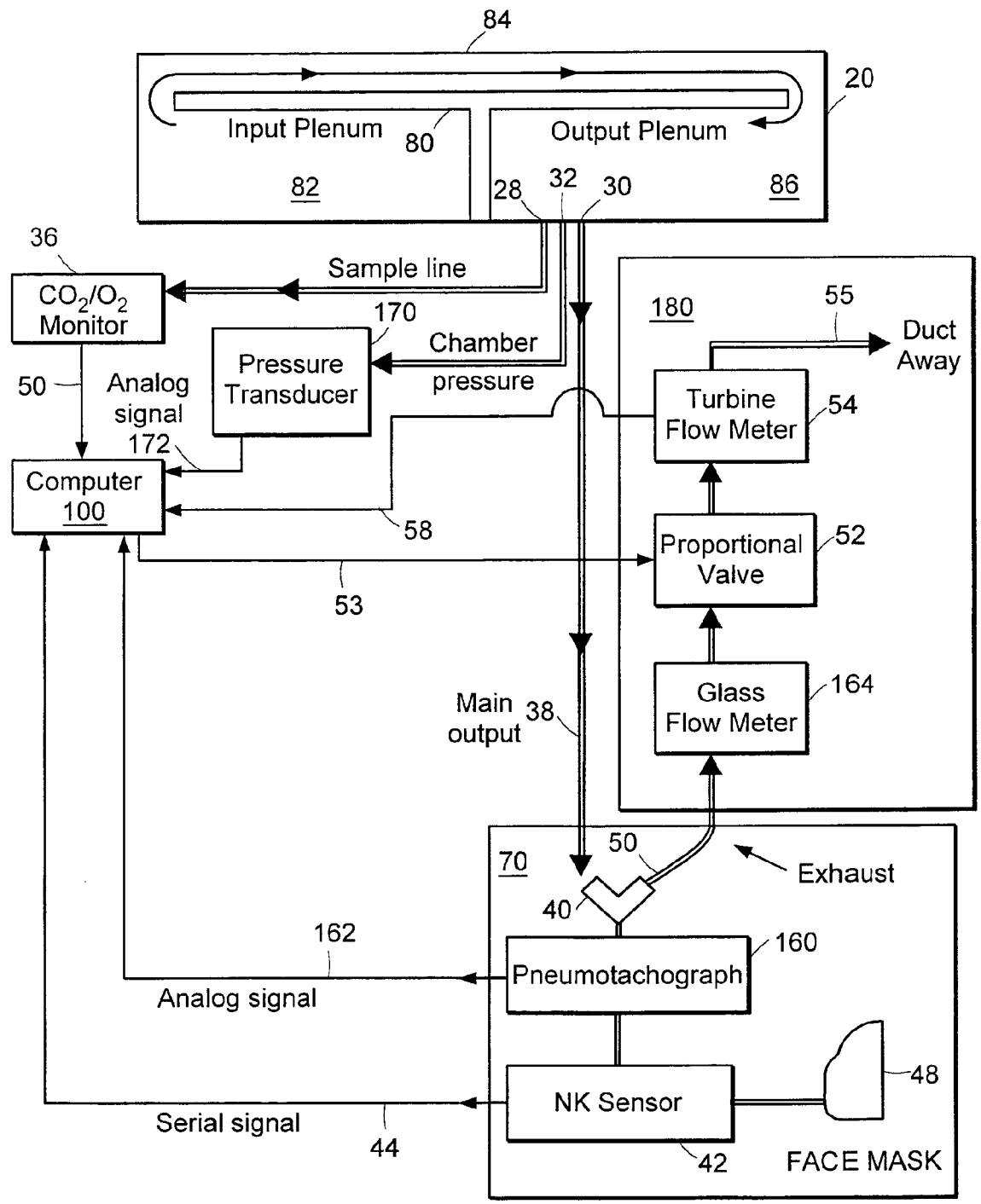
FIG. 2 is a schematic diagram of the output side of an embodiment of the present invention.

FIG. 2 is a schematic diagram of the output side of an embodiment of the invention.

On the output side of the gas mixing module 20 are three output connections 28, 30, 32. In the prototype, these are mounted on the PAPGAM faceplate and include: a ⅛ inch hose barb fitting 28 for connecting a gas-sampling line; a 0.5 inch brass hose barb fitting 32 for measurement of chamber pressure via a connection to a pressure transducer 170; and a standard 22 mm male fitting 30 for hose connection to the breathing/respiratory circuit 70.

A gas sampling monitor or sensor 36, for example, a Datex Capnomac gas monitor, constantly monitors the concentration of oxygen and CO2 in the gas mixing module 20, by sampling the gas in the output plenum 86 via the gas sampling port 28. The gas monitor 36 exports data to the control processor 100 through an analog output, or alternatively, an RS-232 interface (collectively 56). Of course, one skilled in the art would recognize that other formats are also acceptable.

A pressure transducer or manometer 170 measures the pressure of the gas mix within the output plenum 86 via the chamber pressure port 32. Pressure data is then sent to and analyzed by the control processor 100 via signal 172.

Respiratory Circuit

Pressurized air at the proper CO2 and O2 concentrations is supplied from the output plenum 86 of the gas mixing module 20 to the respiratory circuit 70 via an appropriate length of tubing (air supply hose) 38 connected to the main output port 30.

The respiratory circuit 70, including the mask 48, differs from a typical xPAP circuit in several key respects. For example, the mask 48 itself is designed to be as leak-proof as possible, to provide an accurate end-tidal CO2 reading. This has necessitated modifying a standard xPAP mask by sealing the various sources of leaks including the ventilation ports, swivel connections and joints between the mask body and facial pillow.

Furthermore, a CO2 sensor 42 is placed directly in the respiration circuit 70; for example, it may be mounted directly to the surface of the mask 48 by means of a 90-degree swivel fitting (not shown). In one embodiment, this sensor 42 is a Nihon Kohden (NK) TG951T mainstream CO2 sensor, which is compact and lightweight, and which can measure CO2 concentrations in the patient's breath (inhaled or exhaled) at a sampling rate of about 40 Hz. The NK sensor 42 utilizes an infrared spectrometry principle and provides very high resolution, accuracy, and resistance to fogging and clogging. It outputs an RS-232 serial data stream 44 that is received and processed by the control processor 100. The CO2 sensor 42 is the principal means of measuring physiological response to the PAPGAM invention system in real time. Other sensors, capnographs and the like may be used for sensor 42 (for example, Tidal Wave Sp by Novametrix).

The data from the CO2 sensor 42 is, for example, a 9600 baud serial data stream which is received by the control processor 100. WinWedge software (described below) parses the data stream and delivers it via a DDE hotlink to DASYlab.

Finally, a pneumotachograph 160 may be mounted directly to the NK sensor 42. Pressurized air at the proper CO2 and O2 concentrations is supplied to the proximal end of the pneumotachograph 160 by means of a flexible air supply hose with standard female 22 mm adapters on each end. Pneumotachograph 160 is a flow meter, generally of the pitot-tube type. Other types of flow meters are suitable.

Bleed air from the respiratory circuit 70 is exhausted via a return (exhaust) hose 50. The air supply hose 38, bleed air hose 50, and mask/NK/pneumotachograph assembly are connected by a three-way "Y" adapter 40. Thus, a certain amount of deadspace exists between the supply of fresh pressurized air and the patient, but this deadspace is held under 100 ml.

Exhaust System

The exhaust air control system 180 consists of a glass flow meter 164, a proportional valve 52, an electronic turbine meter 54 and exhaust ducting 55.

The glass flow meter 164 allows visual measuring of bleed air from the respiration circuit 70. Bleed air is ducted from the mask 48 to the glass flow meter 164 via the exhaust hose 50.

The proportional valve 52 controls the flow of exhaust, in response to a control signal 53 from the computer 100. This allows the computer to intelligently and dynamically adjust the exhaust flow to compensate for changes over time, for example, should the quality of the of the mask seal change. In another embodiment, exhaust bleed flow is adjusted by means of a manually operated needle valve.

A mask bleed sensor 54 measures flow of the bleed air from the respiratory circuit 70. This sensor 54 may be a turbine flow meter which measures the bleed air after the bleed air passes through the mechanical flowmeter 164. The mask bleed sensor 54 provides an electronic signal 58 to the control processor 100 for analysis, in part to maintain the correct gas mixture.

The bleed air is ducted away from the unit 52 via a length of flexible hose 55 that, in one embodiment, passes out through the rear of the cart.

Control Processor/Signal Interface

FIG. 3 is a schematic diagram of the control processor system.

Signal Interface Unit

The signal interface unit 114 provides an electrical interface between the various sensors incorporated into the invention PAPGAM and the input/output (i.e., data acquisition) circuit board 102 in the control processor 100. The signal interface unit 114 in the prototype consists of the following elements, although it would be recognized by one skilled in the art that functional equivalents could be substituted where appropriate.

1. A steel chassis attached to an aluminum 19" rackmount faceplate;

2. An Iotech DBK201 connection block board 270;

3. An Iotech DBK 207 signal conditioning board 272, which contains 16 slots for inserting 5-B compatible isolated analog signal conditioning modules appropriate to each type of sensor;

4. Cabling connections to appropriate input output connectors at the front and rear of the unit (e.g. DB25, DB9, DB37, front panel jacks);

5. Nine 1.5 mm shielded DIN female panel jacks through-mounted on the faceplate for connection of typical medical sensors;

6. 1¼" front-mounted phono panel jack; and

7. Two ⅛" front-mounted mini phono panel jacks.

The signal interface unit 114 can be configured in a variety of ways to route both digital and analog signals to and from the control processor 100 to various sensors, including the control valve 6, the CO2 flow meter 8, the gas mix monitor 36, the pneumotachographs 160, sound recording equipment 108, as well as other laboratory equipment and sensors 190. The signal interface unit 114 can be configured to accept virtually any type of sensor signal including thermistors, strain gauges, or very low voltage physiological signals such as EEG or EKG signals.

Control Processor (Computer) With Data Acquisition Card

The control processor 100 incorporates a microcomputer and data acquisition card 102. In one embodiment, the microcomputer is an AMD Athlon XP 1800+CPU mounted on an ASUS A7V266 motherboard utilizing the VIA KT-266 chipset. 1 GB of certified EC DDR SDRAM is installed. The computer is housed in an industrial steel 19" 3U high rack mount enclosure incorporating internal and external cooling fans.

Peripherals installed in the computer include:
3.5" Floppy disk drive (not shown);
80 GB 5" ATA hard disk drive (not shown);
CD/RW drive (not shown);
Soundblaster Pro audio card 106;
10/100 mbps ethernet adapter 110;
Logitech wireless USB mouse and keyboard (not shown);
Video adapter card (not shown);
IEEE 1394 (firewire) adapter card (not shown); and
IEEE 1394 compatible removable 40 GB hard drive (not shown).

The control processor 100 is equipped with an Iotech Daq-Board 2000 PCI bus data acquisition circuit board 102. The DaqBoard 2000 is capable of sampling and digitizing 16 single-ended or eight bipolar analog input signals at 200 kilohertz, 16-bit resolution. In addition, it has provision for two analog output signals and forty digital I/O lines, as well as a number of additional counter functions. The Daq2000 card is connected to the DBK 201 board 270 in the signal interface unit 114 by means of a ribbon cable 115.

In a one embodiment, the signal interface unit 114 may be incorporated with the control processor 100 into a single unit.

Display Monitor, 112

In one embodiment, the computer display 112 is a Viewsonic 15" flat panel LCD display that is attached to the PAPGAM cart by a flexible monitor arm (not shown).

Software

In one embodiment, the control processor 100 runs under the Windows XP Professional operating system. The principle application providing control of the invention system (PAPGAM) is National Instruments DASYlab version 7.0. DASYlab provides a complete development and runtime environment for creating complex monitoring and control systems. A custom "worksheet" and screen display has been created within DASYlab that provides for monitoring of all instrument functions.

Low-level and DASYlab drivers for the DaqBoard 2000 and DBK 207 boards 102, 272 are loaded under Windows XP.

While most sensors attached to the invention system communicate directly with the Iotech DaqBoard 2000 card 102 via an analog signal, several sensors communicate with DASYlab via DDE (Microsoft Dynamic Data Exchange) data transfer under Windows XP. In order to implement this DDE transfer and create a flexible platform for incorporating additional serial data streams, an RS-232 wedge application is available to run under Windows XP. TALtech Technologies WinWedge Pro is a serial data acquisition program that can be configured to act as a DDE server. For each sensor that communicates with the PAPGAM via RS-232 serial interface there is a separate DB-9 connector at the back of the computer enclosure and a custom interface has been written. Within DASYlab, it is possible to configure a data module that acts as a DDE client and that queries WinWedge Pro for the values of selected data fields.

The PAPGAM can also be configured to be a complete post-acquisition review workstation. To this end, National Instruments' DIAdem, running under Windows XP, provides both data review and visualization capabilities as well as sophisticated signal processing and mathematical manipulation features.

The invention system (PAPGAM) is controllable remotely from another workstation via a wireless (or alternatively, wired) TCP/IP connection 110 using the Remote Desktop feature of Windows XP Professional. A LinkSys USB wireless Ethernet receiver/transmitter performs this function.

An embodiment of the PAPGAM also incorporates a highly sophisticated digital audio recording and analysis package 106, such as Cakewalk Sonar II, which provides multi-track digital recording, filtering visualization and playback. Sensitive microphones 108 attached to the patient can be connected through the signal interface module 114 and/or the Soundblaster card for recording under Sonar II.

Housing/Enclosure

In a prototype model, and in an embodiment intended for office use, a steel rackmount enclosure measuring 19" wide by 19" deep by 36" high for example, is mounted on lockable caster wheels. The gas mixing module 20 and the control processor 100 are mounted in the enclosure or cart.

In other, more portable embodiments, the enclosure may consist of a relatively small and lightweight unit.

Physiological Sensors

The control processor 100/signal interface 114 can accept input from virtually any type of physiological sensor able to output an analog or digital signal. For example, embodiments of the present invention may include some or all of the following types of physiological sensors as part of the overall invention system (PAPGAM) montage. While specific brands and models are listed, it would be understood by one skilled in the art that other models by other manufacturers which perform essentially the same functions could be substituted.

For example, a transcutaneous blood gas monitor (not shown), such as the advanced Sensormedics Microgas 7650 transcutaneous blood gas monitor or Novametrix TCO2M transcutaneous monitor, or the like, can provide non-invasive measurement of arterial partial pressure of oxygen and CO2. It utilizes a heated surface probe that is attached to the patient via a disposable adhesive circular strip. The unit is self-calibrating and has data ports for both serial and analog outputs. This unit can be used in conjunction with the invention PAPGAM system in a clinical setting for safety, diagnostic and titration purposes.

Furthermore, in one embodiment of the present invention, a Braebon Ultima Plus Dual Channel Pressure Sensor (not shown) and Datex-Ohmeda D-Lite Pneumotachograph 160 (FIG. 2) can work in conjunction in a variety of possible configurations to provide the PAPGAM with air flow and pressure data. In one embodiment, the pneumotachograph 160 is mounted in proximity to the patient mask 48 to provide data about inspired and expired breath volume. The Braebon unit interprets the pressure data from the D-Lite sensor and outputs two analog voltage signals 162 which represent the flow and pressure data. These are routed to the signal interface unit 114 via mini audio jacks located on the front panel.

Principle of Operation

The PAPGAM prototype has been designed for use principally during a sleep study to determine the appropriate prescription for CO2 gas and O2 gas in conjunction with xPAP therapy for patients suffering from periodic breathing.

Although a patient would ordinarily be instrumented as for a typical sleep study, such a step may not be necessary given the capabilities of the invention PAPGAM. In addition to the usual instrumentation, which can be recorded separately, the PAPGAM sensors, including the Sensormedics transcutaneous unit, the NK sensor, the D-Lite/Braebon sensors, etc., can be applied to the patient.

Once the study has begun, a clinician can select an initial setpoint for the PAPGAM, expressed in percent CO2.

Prior to initiating recording, the PAPGAM will prompt the clinician for a number of data items, including patient information and alarm limits for a number of parameters, such as:
1. Maximum CO2 flow
2. Maximum inspired CO2 (measured by the NK sensor 42)
3. Maximum arterial CO2 (measured by the Sensormedics Sensor)
4. Maximum concentration of CO2 in the mixing chamber 20

Figure 4:
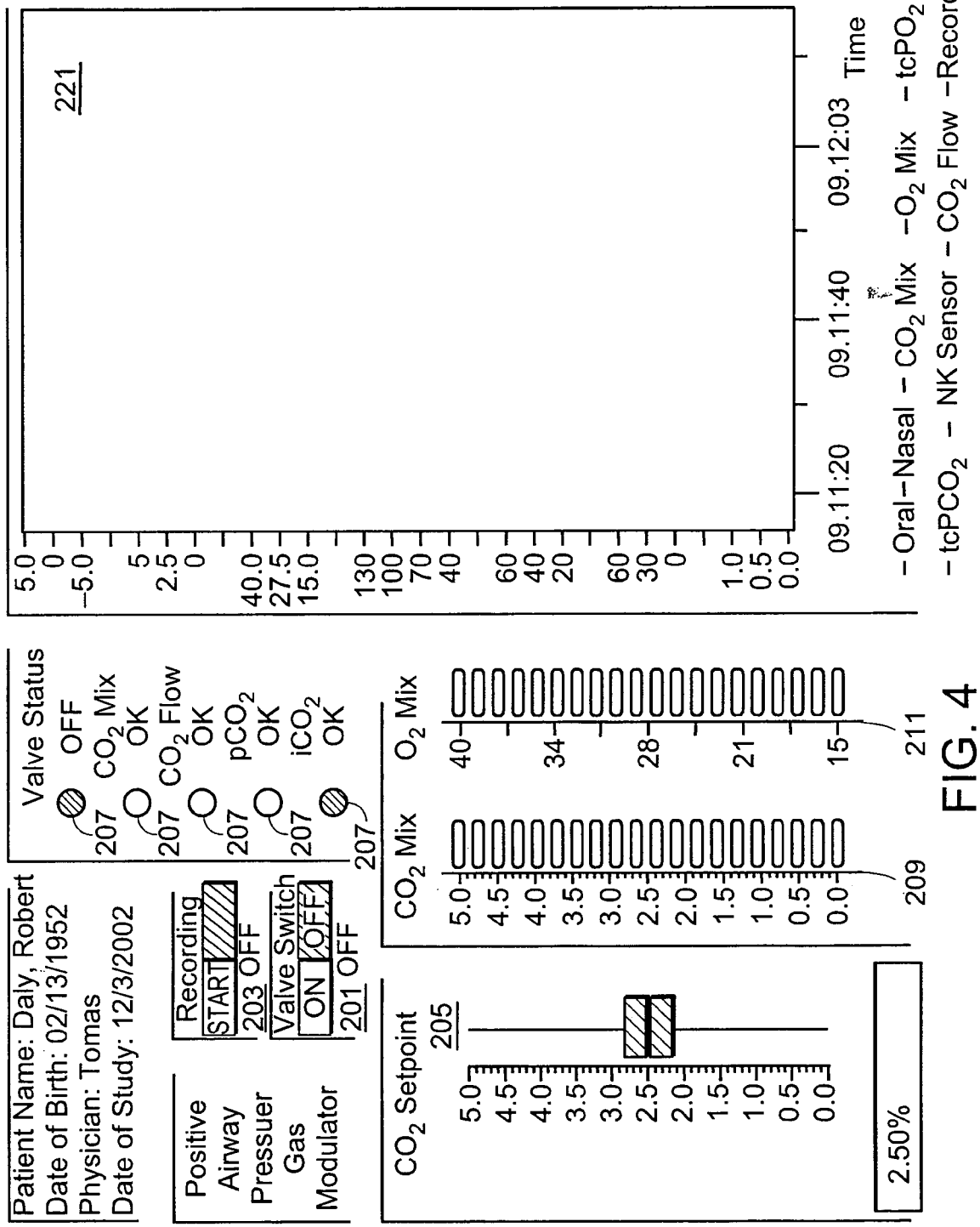
FIG. 4 illustrates a sample display screen of an embodiment of the present invention.

FIG. 4 illustrates a sample display screen 500. The clinician can initiate recording from the main display screen 500 by selecting (e.g., clicking on) a screen button 203. Once recording has been initiated and all other clinical procedures are complete, the clinician initiates delivery by adjusting the CO2 setpoint by moving the software slider 205 up or down and turning on the valve 6 switch (software button 201).

At a frequency of 12 Hz, DASYlab evaluates incoming data for detection of alarm states. Should any of the input parameters be exceeded, an alarm condition will be called and an indicator 207 will turn red on the screen. The existence of any alarm state may cause the control valve 6 (FIG. 1) to shut off or reduce flow of CO2 until the alarm state is cleared, or they may simply notify the operator of the existence of an alarm condition.

Two software level indicators 209, 211 display the actual percent CO2 and percent O2 concentrations respectively, which are sampled from the output plenum 86 of the gas mixing module 20, providing visual verification that the gas mix remains at the target concentration.

A scrolling chart recorder 221 can display various parameters of interest, including CO2 mix, O2 mix, valve state, physiological signals being received and so forth.

As the study progresses, the clinician may wish to change the CO2 dosage. This is accomplished by adjusting the CO2 setpoint with the software slider 205, and visually monitoring the change in gas mix at 209, 211. A further embodiment may include an audio alarm at the nursing station to alert personnel as to any alarm state, including an underdose.

Finally, all parameters are stored in a file in proprietary DASYlab format. These files can be further analyzed and processed post-study. They can also be output in a variety of formats for display and analysis in other applications.

Other Papgam Embodiments

The embodiment described above is primarily designed to be a tool for clinical investigation, and as such it incorporates functionality which may not be necessary for some classes of commercially available products. Two such product embodiments are now described.

PAPGAM CLINICAL: A clinical PAPGAM embodiment is intended for use primarily in a clinical setting, particularly a sleep laboratory. It permits operator adjustment of CO2 and air bleed parameters, can record detailed information as does the current prototype, and can output reports in set formats. The unit may have a "cart" form factor (housing) and may be remotely operable.

PAPGAM HOME: A "home" unit embodiment is intended for a non-clinical setting, such as a patient's home. The home unit is not user adjustable, but can be programmed by a home care technician according to a physician's prescription. It has a simple on/off switch and a number of status indicators. The CO2 source can be incorporated directly into the unit by means of a screw-in type canister or it can be connected via tubing. The canister itself may have an orifice sized to limit flow to a maximum specification. The home unit may incorporate simplified recording and reporting capabilities which are accessible remotely by a clinician, e.g., via a dial-up connection. This unit can have a form factor that is as compact as possible, preferably a bedside tabletop size that fits under the patient's xPAP unit.

Variable Deadspace Mask

Figure 5:
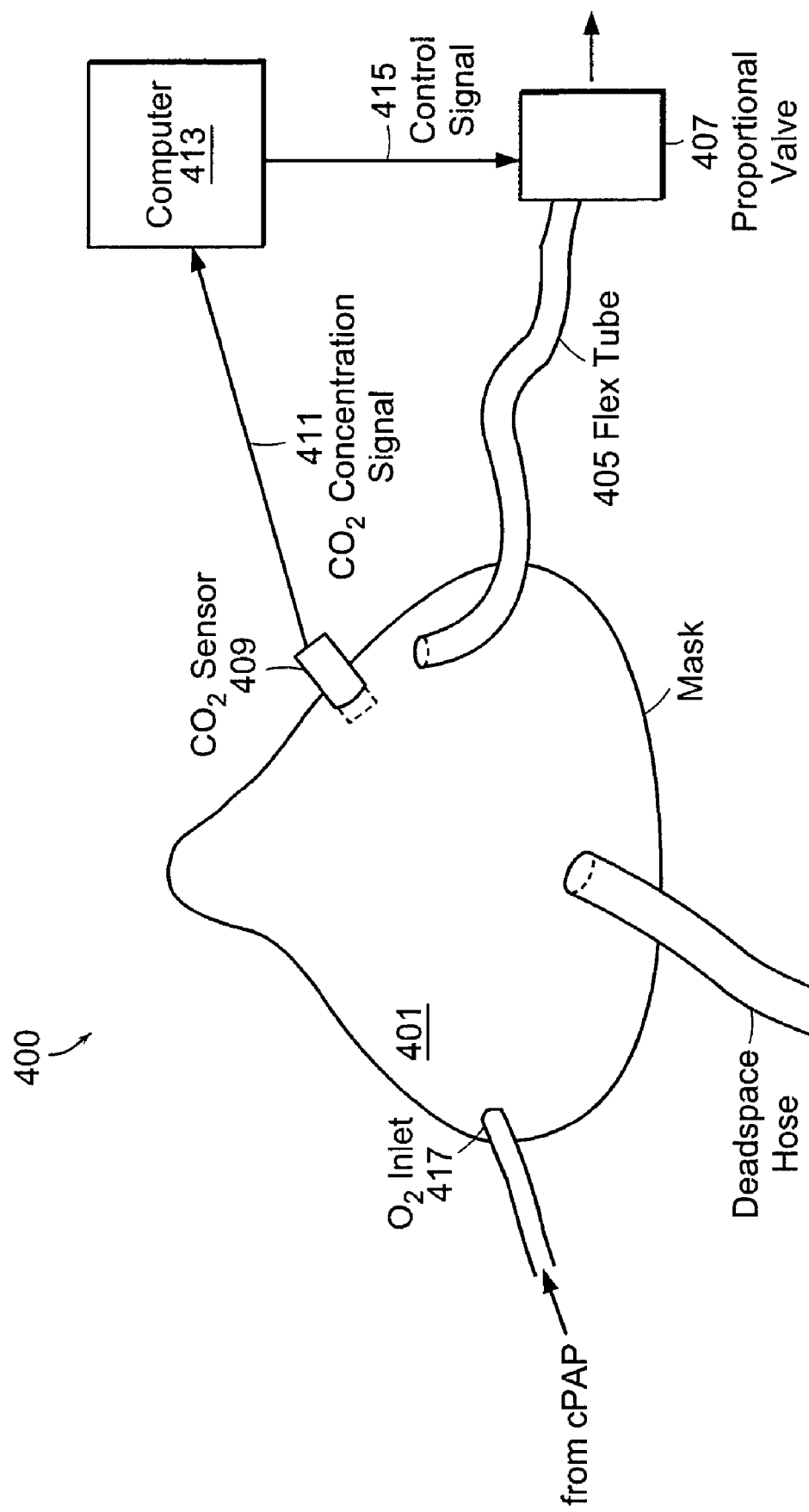
FIG. 5 is a schematic diagram of a variable deadspace embodiment of the present invention.

FIG. 5 is a schematic diagram of a variable deadspace embodiment 400 of the present invention.

One purpose of this embodiment of the present invention is to raise the CO2 concentration of air being delivered from a cPAP machine to a target value without the use of supplemental CO2. This is accomplished by causing the patient to rebreathe his own CO2 from a reservoir (deadspace) 403 attached to a mask 401.

The reservoir 403 may, for example, consist of a length of hose (the deadspace hose) with a capacity of approximately 500 ml. Ordinarily, no air should leak from the deadspace hose/mask combination.

The patient's own CO2 is accumulated in this reservoir 403, so he rebreathes it. When the average inspired concentration of CO2 from the hose/mask combination begins to exceed the desired level, the average concentration of inspired CO2 is limited by permitting air to be vented out of the mask 401, for example at inlet 417, down through a flexible tube 405 and out through a variable orifice. The variable orifice may comprise, for example, a small proportional valve 407 operated by a computer 413 that receives CO2 concentration information 411 from a CO2 sensor 409, for example, the same type of mainstream (Nihon Kohden) CO2 sensor discussed previously.

Thus, as CO2 is rebreathed from the deadspace 403, the sensor 409 monitors the CO2. Once the CO2 concentration reaches the desired target level, the valve 407 begins to open in order to keep the CO2 concentration from going over target level. To prevent depletion of oxygen in the deadspace, a small amount of O2 may be introduced into the breathing circuit, for example, either directly into the mask (as shown at 417), or alternatively, on the side of the deadspace hose 403 closest to the cPAP.

The concentration of CO2 in the deadspace 403 will be on a gradient (highest at the mask, lowest at the interface with the cPAP). As the patient breathes in the air accumulated in the deadspace 403, the concentration will change. A computational algorithm is executed by the computer 413 to determine average inspired CO2, so that the desired level may be sustained.

Periodic Breathing Embodiment

Periodic breathing in a patient tends to have a fairly fixed-time component. That is, the actual period of the oscillations is generally determined by physiological conditions that are reasonably fixed in the short term. Hence, any periodic breathing patient tends to have well-defined cycles. Incidentally, the principal determinant is the amount of time that it takes for changes in carbon dioxide levels to be sensed by the brain. The breathing period tends to be about double that time. In most congestive heart failure patients, this results in an apnea-to-apnea period of approximately a minute and a half.

Thus, an embodiment of the invention can detect, using the NK sensor 42 (FIG. 2), where the patient is in the breathing cycle, and apply CO2 only at the appropriate time, e.g., when CO2 levels are dropping. The effect is to abort the problematic breathing cycle altogether.

An advantage to this approach is the ability to deliver CO2 to a patient who is not even on positive airway pressure, for example a waking congestive heart failure patient who is using a typical oxygen cannula. During a short part of the cycle, the periodic breathing can be aborted by injecting CO2 during inspiration for as few as three or four breaths. In this case, the CO2 concentration may not be as critical, since CO2 is injected into the airway circuit for only a short time.

This falls under the heading of physiological closed loop control, but builds on existing knowledge about the mathematics of periodic breathing. See, for example, Francis et al., "Quantitative General Theory for Periodic Breathing in Chronic Heart Failure and its Clinical Implications", Circulation, 102(18):2214-2221, Oct. 31, 2000, which is a treatise on the mathematics of periodic breathing and which is incorporated by reference herein in its entirety. Note particularly graph 6B of the Francis paper, which sets forth the interventions, which are effective in restoring stability to a PB patient. It indicates that oxygen and CO2 most directly restore stability.

This embodiment might not include positive airway pressure, and the exact mix of CO2 may not be important. In fact, the delivery mechanism might be as simple as injecting CO2 in high concentrations into a loose-fitting facemask in a manner timed to coincide with the inspiration of a few breaths.

Sudden Infant Death Syndrome

The inventors believe that Sudden Infant Death Syndrome (SIDS) is a form of, or is related to, periodic breathing, and therefore may be preventable with PAPGAM. While direct application to SIDS children is obviously impractical as SIDS children are not generally identified in advance, there is a class of children who have had an "Apparent Life Threatening Experience" (ALTE), who may benefit from prophylactic measures for the few months before their respiratory systems mature and the risk of SIDS is reduced.

In addition, there is a condition known as "apnea of prematurity", which may also be treatable with the invention PAPGAM system.

Thus, the PAPGAM may be useful in neonatal applications for inducing respiratory stability in this class of patients. Specifically, a PAPGAM may be connected to a patient centric ventilatory space module (PCVSM), such as an incubator, tent, facemask, nasal cannula, or similar device, with or without positive airway pressure. In the case of a tent or incubator, the gas might be sampled not from the mixing box, but rather from the incubator itself, or from both.

While this invention has been particularly shown and described with references to preferred embodiments thereof, it will be understood by those skilled in the art that various changes in form and details may be made therein without departing from the scope of the invention encompassed by the appended claims.

For example, given the low effective concentrations of CO2 discovered by Applicants, some embodiments will not employ a gas mixing module 20 of FIG. 1 but rather will achieve the proper combination of PAP (pressurized air) and CO2 in some other means or in the PCVSM subsystem or the like.

Respiratory instability may be caused by a variety of conditions such as sleep apnea, renal failure, congestive heart failure and other conditions. It is understood from the foregoing discussion hat the present invention is applicable to each of these conditions.

What is claimed is:

1. A positive airway pressure (PAP) device for stabilizing breathing during sleep comprising
    a PAP device for sleep therapy, the PAP device further comprising
    a source of medical grade carbon dioxide;
    an assembly for combining pressurized air from the PAP device with substantially low concentrations of the medical grade carbon dioxide resulting in a gas mix; and
    a patient centric ventilatory space module (PCVSM) coupled to the assembly providing the resulting gas mix for inhalation by a given target, said inhalation of the gas mix effecting respiratory stability of said target
    wherein concentration of carbon dioxide in the gas mix is less than 2%.

2. A device as claimed in claim 1 wherein the assembly includes a sensor for measuring air flow.

3. A device as claimed in claim 1 wherein the PCVSM includes any of:
    a facemask, and a nasal cannula.

4. A device as claimed in claim 1 wherein concentration of carbon dioxide in the gas mix is between about 0.5% and about 1.25%.

5. A positive airway pressure (PAP) device for stabilizing breathing during sleep comprising
    a PAP device for sleep therapy, the PAP device further comprising
    a source of medical grade carbon dioxide;
    an assembly for combining pressurized air from the PAP device with substantially low concentrations of the medical grade carbon dioxide resulting in a gas mix; and
    a patient centric ventilatory space module (PCVSM) coupled to the assembly providing the resulting gas mix for inhalation by a given target, said inhalation of the gas mix effecting respiratory stability of said target
    wherein at least one of the source, the assembly and the PCVSM is computer processor controlled to modulate concentration of carbon dioxide in the gas mix and the computer processor modulates concentration of $CO_2$ in the gas mix as a function of any combination of sensed concentration of carbon dioxide in the PCVSM, sensed target state and detected system changes.

6. A method for preparing a gas mix for enabling respiratory stability for a positive airway pressure (PAP) device for sleep therapy, comprising the steps of:
    providing a substantially low concentration of medical grade carbon dioxide to a PAP device used for sleep therapy;
    combining pressurized air from the PAP device used for sleep therapy with the medical grade carbon dioxide to form a gas mix having stabilizing effects on breathing, the pressurized air enabling the carbon dioxide at low concentrations in the gas mix to have stabilizing effects on target respiratory systems; and
    delivering the gas mix to a subject with the PAP device used for sleep therapy.

7. The method of claim 6 wherein the step of combining includes employing positive airway pressure.

8. The method of claim 6 wherein the step of combining includes utilizing a face mask worn by a target patient.

9. The method of claim 6 wherein the step of providing includes employing carbon dioxide at concentrations of less than 2%.

10. The method of claim 6 wherein the step of providing includes employing carbon dioxide at concentrations in the range of about 0.5% and about 1.25%.

11. A device for stabilizing breathing comprising a source of medical grade carbon dioxide;
    an assembly for combining pressurized air from a positive airway pressure PAP device with substantially low concentrations of the medical grade carbon dioxide resulting in a gas mix; and a patient centric ventilatory space module (PCVSM) coupled to the assembly providing the resulting gas mix for inhalation by a given target, said inhalation of the gas mix effecting respiratory stability of said target wherein at least one of the source, the assembly and the PCVSM is computer processor controlled to modulate concentration of carbon dioxide in the gas mix and the computer processor modulates concentration of $CO_2$ in the gas mix as a function of any combination of sensed concentration of carbon dioxide in the PCVSM, sensed target state and detected system changes.

12. A device for stabilizing breathing comprising a source of medical grade carbon dioxidel;

an assembly for combining pressurized air from a positive airway pressure PAP device with substantially low concentrations of the medical grade carbon dioxide resulting in a gas mix; and a patient centric ventilatory space module (PCVSM) coupled to the assembly providing the resulting gas mix for inhalation by a given target, said inhalation of the gas mix effecting respiratory stability of said target wherein at least one of the source, the assembly and the PCVSM is computer processor controlled to modulate concentration of carbon dioxide in the gas mix and the computer processor continuously receives and analyzes incoming data and indicates an alarm condition based on the incoming data and at least one of the following parameters:

maximum first gas flow;

maximum inspired first gas;

maximum arterial $CO_2$;

maximum end tidal carbon dioxide; and maximum percent first gas in the mixing means, the computer processor stopping or reducing delivery of the first gas when an alarm condition is present.

13. A device for stabilizing breathing comprising a source of medical grade carbon dioxide;

an assembly for combining pressurized air from a positive airway pressure PAP device with substantially low concentrations of the medical grade carbon dioxide resulting in a gas mix; and a patient centric ventilatory space module (PCVSM) coupled to the assembly providing the resulting gas mix for inhalation by a given target, said inhalation of the gas mix effecting respiratory stability of said target wherein at least one of the source, the assembly and the PCVSM is computer processor controlled to modulate concentration of carbon dioxide in the gas mix and the computer processor controls concentration of $CO_2$ for a patient diagnosed as having sleep disordered breathing (SDB).

14. A device for stabilizing breathing comprising a source of medical grade carbon dioxide;

an assembly for combining pressurized air from a positive airway pressure PAP device with substantially low concentrations of the medical grade carbon dioxide resulting in a gas mix; and a patient centric ventilatory space module (PCVSM) coupled to the assembly providing the resulting gas mix for inhalation by a given target, said inhalation of the gas mix effecting respiratory stability of said target wherein at least one of the source, the assembly and the PCVSM is computer processor controlled to modulate concentration of carbon dioxide in the gas mix;

the source of the carbon dioxide is a pressurized source; and the gas modulation system further comprises a control value module which regulates flow of the carbon dioxide from the pressurized source to the assembly, the control valve module responding to a control signal from the computer processor; and the control valve module comprises a solenoid valve or a proportional valve.

* * * * *